United States Patent [19]
Gono et al.

[11] Patent Number: 5,873,826
[45] Date of Patent: Feb. 23, 1999

[54] FLUOROSCOPY METHOD AND X-RAY CT APPARATUS

[75] Inventors: Makoto Gono; Yasuro Takiura, both of Tokyo, Japan

[73] Assignee: GE Yokogawa Medical Systems, Limited, Tokyo, Japan

[21] Appl. No.: 893,652

[22] Filed: Jul. 11, 1997

[30] Foreign Application Priority Data

Jul. 19, 1996 [JP] Japan .................................. 8-190438

[51] Int. Cl.$^6$ ......................................................... A61B 5/05
[52] U.S. Cl. .......................... 600/425; 250/360; 378/62; 378/97
[58] Field of Search ..................................... 600/407, 425; 378/62, 64, 65, 68, 15, 4, 11, 13, 97, 114, 117, 140, 161; 250/360.1, 370.08, 370.09

[56] References Cited

U.S. PATENT DOCUMENTS

| | | |
|---|---|---|
| 4,107,531 | 8/1978 | Garratt et al. .......................... 250/360 |
| 4,274,005 | 6/1981 | Yamamura et al. ..................... 250/419 |
| 4,993,404 | 2/1991 | Lane . |
| 5,127,394 | 7/1992 | Lane . |
| 5,185,788 | 2/1993 | Magram . |
| 5,253,169 | 10/1993 | Corby . |
| 5,265,144 | 11/1993 | Harding et al. ........................... 378/86 |
| 5,265,610 | 11/1993 | Darrow . |
| 5,379,333 | 1/1995 | Toth . |
| 5,602,889 | 2/1997 | Oldendorf et al. ....................... 378/29 |

FOREIGN PATENT DOCUMENTS

| | | |
|---|---|---|
| 0545588 | 6/1993 | European Pat. Off. . |
| 9100056 | 10/1991 | WIPO . |

*Primary Examiner*—Brian Casler
*Attorney, Agent, or Firm*—Moonray Kojima

[57] ABSTRACT

To make it possible to decrease an X-ray exposure on an operator and to obtain an image of high quality upon fluoroscopy operation an X-ray tube is rotated to acquire data, an X-ray radiation dose is set to "0" in a predetermined angular range including an angle at which the alignment of the X-ray tube with the operator's hand is brought about, and the X-ray radiation dose is set to an ordinary one at an angle in a range other than that angular range. The predetermined angular range is established using a light beam which enables to see what part of the field has no X-ray radiation exposure, thereby increasing his safety.

5 Claims, 6 Drawing Sheets

FLUOROSCOPY METHOD AND X-RAY CT APPARATUS

FIELD OF THE INVENTION

The present invention relates to a fluoroscopy method and an X-ray CT (Computed Tomography) apparatus, and more particularly, to a fluoroscopy method and an X-ray CT apparatus in which it becomes possible to protect an operator from intensive exposure to the X-ray radiation while obtaining an image of high quality as the fluoroscopy is carried out.

BACKGROUND OF THE INVENTION

Figure 1:
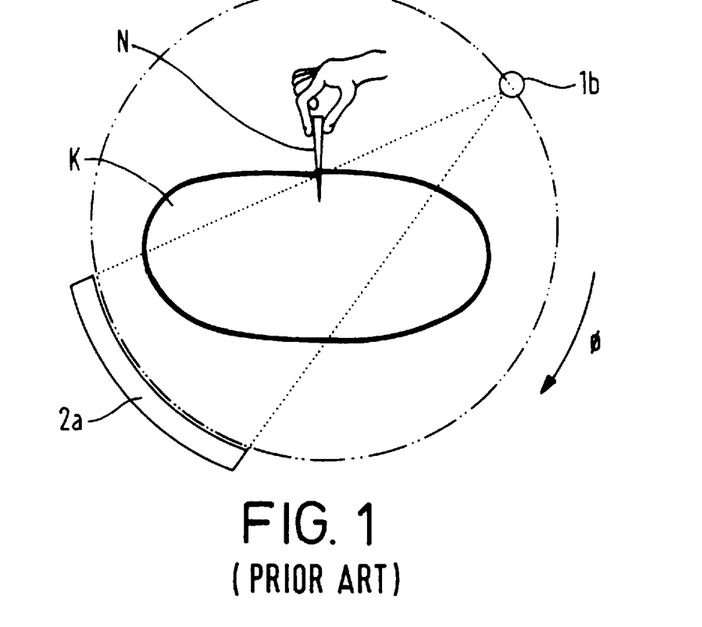
FIG. 1 is a diagram useful for explaining the conventional rotation of an X-ray tube and an X-ray detector.

When a fluoroscopy is performed with an X-ray CT apparatus, as shown in FIG. 1, during which an X-ray tube 1b and an X-ray detector 2a are rotated to acquire data for producing an image, an operator stabs a biopsy needle N into a subject K.

Figure 2:
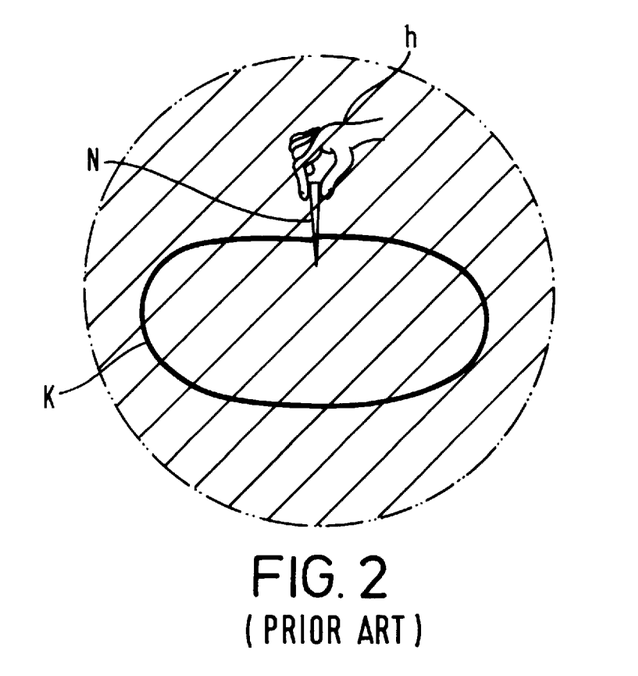
FIG. 2 is an explanatory diagram of a space through which an X-ray passes during one rotation of the X-ray tube and the X-ray detector in a conventional X-ray CT apparatus.

A hatched region in FIG. 2 represents a space through which the X-ray passes during one rotation of the X-ray tube 1b and the X-ray detector 2a. As will be understood from FIG. 2, there is a problem in that the operator is exposed to the X-ray because the operator's hand lies in the space through which the X-ray passes.

In order to decrease an X-ray radiation dose to which the operator is exposed, it is desirable to set the X-ray radiation dose low. However, this will cause another problem in that data cannot be acquired with a good S/N ratio and the image quality is deteriorated.

SUMMARY OF THE INVENTION

It is therefore a general object of the present invention to provide a fluoroscopy method and an X-ray CT apparatus in which the above-mentioned drawbacks and shortcomings are eliminated.

It is a more specific object of the present invention to provide a fluoroscopy method and an X-ray CT apparatus in which it becomes possible to protect an operator from intensive exposure to the X-ray radiation while obtaining an image with high quality as the fluoroscopy is carried out.

According to one aspect of the present invention, there is provided a fluoroscopy method in which an X-ray tube is rotated around the subject to acquire data by an X-ray detector and a data acquisition system thereby to produce an image, and a biopsy needle is stabbed into a subject by an operator's hand, wherein an X-ray radiation dose when alignment of the X-ray tube with the operator's hand is brought about is set to "0" or lower than an X-ray radiation dose when alignment of the X-ray tube with the subject but without the operator's hand is brought about.

When the X-ray tube and the operator's hand are arrayed in this order the operator's hand would, in the prior art, be directly exposed to the X-ray radiation. However, the X-ray radiation dose in this invention is set to "0" or low and hence the X-ray exposure of the operator is small. On the other hand, when the X-ray tube and the subject without the operator's hand are arrayed in this order the X-ray radiation dose is increased. However, the operator's hand is not directly exposed to the X-ray because the hand lies outside or behind the subject, and the X-ray exposure of the operator is also small. Therefore, the operator is less exposed to the X-ray radiation.

When the X-ray tube lies in an angular range in which the alignment of the X-ray tube and the subject and without the operator's hand is brought about, the X-ray radiation dose becomes increased. Therefore, it is possible to acquire data with a good S/N ratio and obtain an image of high quality.

According to a second aspect the present invention, there is provided an X-ray CT apparatus in which an X-ray tube is rotated around a subject to acquire data by an X-ray detector and a data acquisition system and a reconstruction operation is effected on the data to produce an image, comprising X-ray radiation dose control means for changing an X-ray radiation dose depending on an angle in one rotation of the X-ray tube.

According to the X-ray CT apparatus of the second aspect, the X-ray radiation dose control means changes the X-ray radiation dose so that the X-ray radiation dose is set to "0" or relatively low at an angle where an alignment of the X-ray tube and the operator's hand is brought about, while the X-ray radiation dose is set relatively high at an angle where the alignment of the X-ray tube and the subject but without the operator's hand is brought about. Therefore, it is possible to put into practice the fluoroscopy method according to the above-described first aspect and hence the operator can be protected from intensive X-ray exposure when the fluoroscopy is carried out. Also, an image of high quality can be obtained.

According to a third aspect of the present invention, there is provided an X-ray CT apparatus in which an X-ray tube is rotated around a subject to acquire data by an X-ray detector and a data acquisition system and a reconstruction operation is effected on the data to produce an image, comprising X-ray radiation dose control means for setting the X-ray radiation dose to "0" or relatively low when the X-ray tube lies in a predetermined angular range and setting the X-ray radiation dose relatively high when the X-ray tube lies in an angular range other than that angular range.

According to the X-ray CT apparatus of the third aspect, if the angular range is specified so as to include an angle where the alignment of the X-ray tube and the operator's hand is brought about, the X-ray radiation dose is set to "0" or relatively low at the angle where the alignment of the X-ray tube and the subject is brought about, and the X-ray radiation dose becomes relatively high at an angle where the alignment of the X-ray tube and the subject without the operator's hand is brought about. Therefore, the fluoroscopy method according to the first aspect can be suitably practiced. That is, the X-ray exposure of the operator can be decreased upon fluoroscopy operation. Also, an image of high quality can be obtained.

According to a fourth aspect of the present invention, there is provided an X-ray CT apparatus in which an X-ray tube is rotated around a subject to acquire data by an X-ray detector and a data acquisition system and a reconstruction operation is effected on the data to produce an image, comprising angular range specifying means for specifying an angular range in one rotation of the X-ray tube, X-ray radiation dose control means for setting the X-ray radiation dose to "0" or relatively low when the X-ray tube lies in that said angular range while setting the X-ray radiation dose to relatively high when the X-ray tube lies in an angular range other than that angular range, reference light means for indicating with light a range in which the X-ray radiation is effected, and reference light control means for varying the light from the reference light so as to provide information concerning whether the X-ray tube lies in said angular range or not.

According to the X-ray CT apparatus of the fourth aspect, if the operator operates the angular range specifying means so that the angular range includes an angle where the alignment of the X-ray tube and the operator's hand brought about, then the X-ray radiation dose is set to "0" or relatively low at the angle where the alignment of the X-ray tube and the subject is brought about, and the X-ray radiation dose is set to relatively high at an angle where the alignment of the X-ray tube and the subject without the operator's hand is brought about. Therefore, the fluoroscopy method according to the first aspect can be suitably practiced. That is, the X-ray exposure of the operator can be decreased upon the fluoroscopy operation. Also, an image of high quality can be obtained.

Moreover, by variation of the light from the reference light means (variation in brightness and/or in hue), it can be determined whether the X-ray tube lies in said angular range or not. Thus, the operator can accurately specify the angular range in which the X-ray exposure is decreased. Also, the operator can easily be informed of a position where the hand will be less exposed to the X-ray radiation.

Further objects and advantages of the present invention will be apparent from the following description of the preferred embodiments of the invention as illustrated in accompanying drawings.

DETAILED DESCRIPTION OF THE PREFERRED EMBODIMENTS

The invention will hereinafter be described in more detail based on the mode for carrying out the invention with reference to the accompanying drawings. It is to be understood that the invention should not be restrictively interpreted by the following description.

Figure 3:
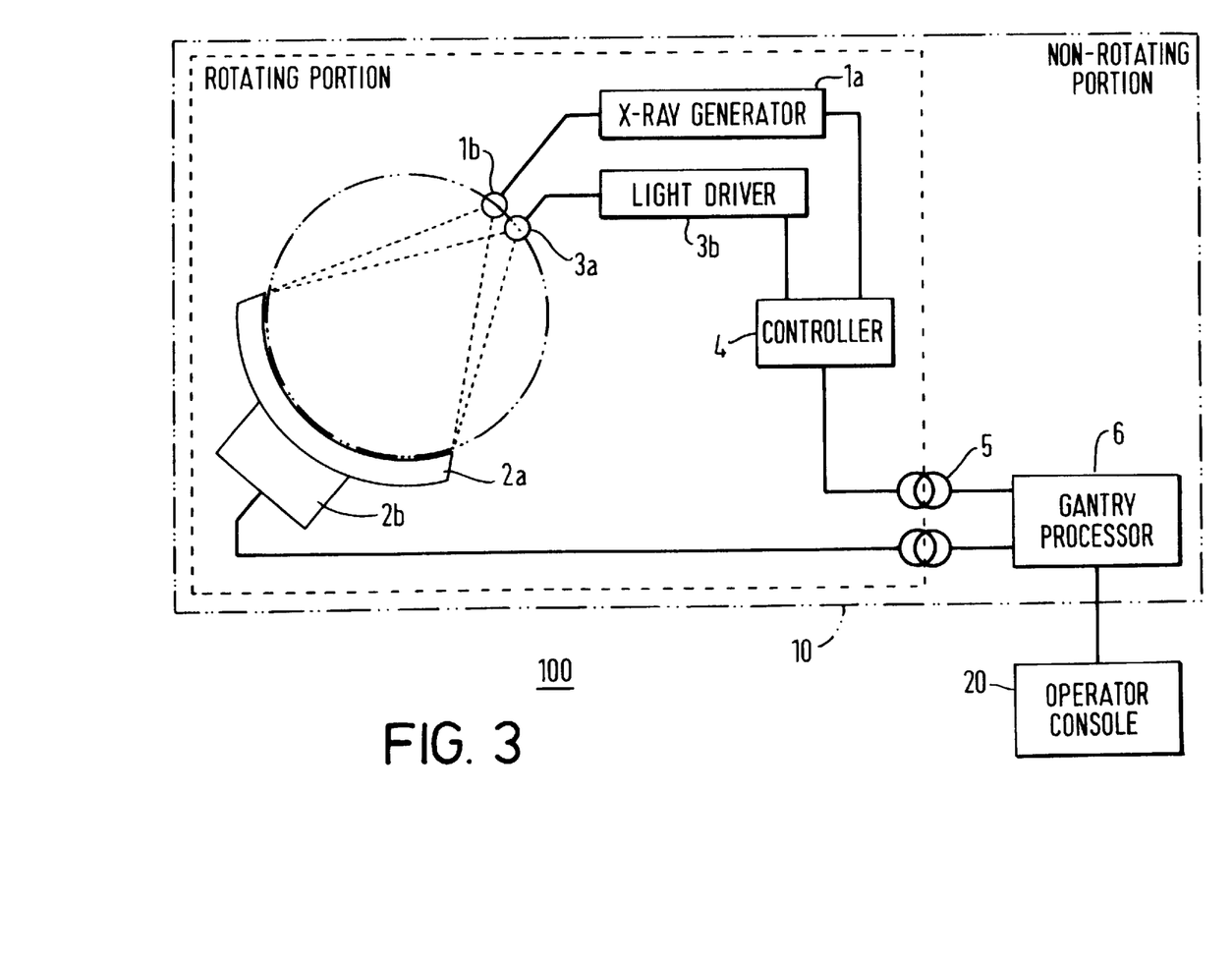
FIG. 3 is a diagram showing an arrangement of a main portion of an X-ray CT apparatus according to one mode of the present invention.

FIG. 3 is a diagram showing an arrangement of a main portion of an X-ray CT apparatus in which one mode of the present invention is carried out.

An X-ray CT apparatus 100 includes a gantry 10 and an operator console 20.

The gantry 10 includes an X-ray generator 1a and an X-ray tube 1b for irradiating X-ray onto a subject (reference symbol K in FIG. 7), an X-ray detector 2a and a data acquisition system 2b for detecting the X-ray having penetrated the subject and acquiring data, a reference light 3a and a light driver 3b for indicating with light a space through which the X-ray passes, a controller 4 for controlling the X-ray generator 1a and the light driver 3b, a slip ring 5 for electrically coupling a rotating portion to a non-rotating portion, and a gantry processor 6 for communicating with the operator console 20. The light driver 3b controls the timing, intensity, directivity and position of light 3a.

The operator console 20 includes a reconstruction processor for reconstructing an image (tomography) from the data, a storage device for storing the data, image or the like, an image display for displaying the image or message, an input device for an operator to input a command, a parameter or the like, and a CPU for performing the overall control.

Figure 4:
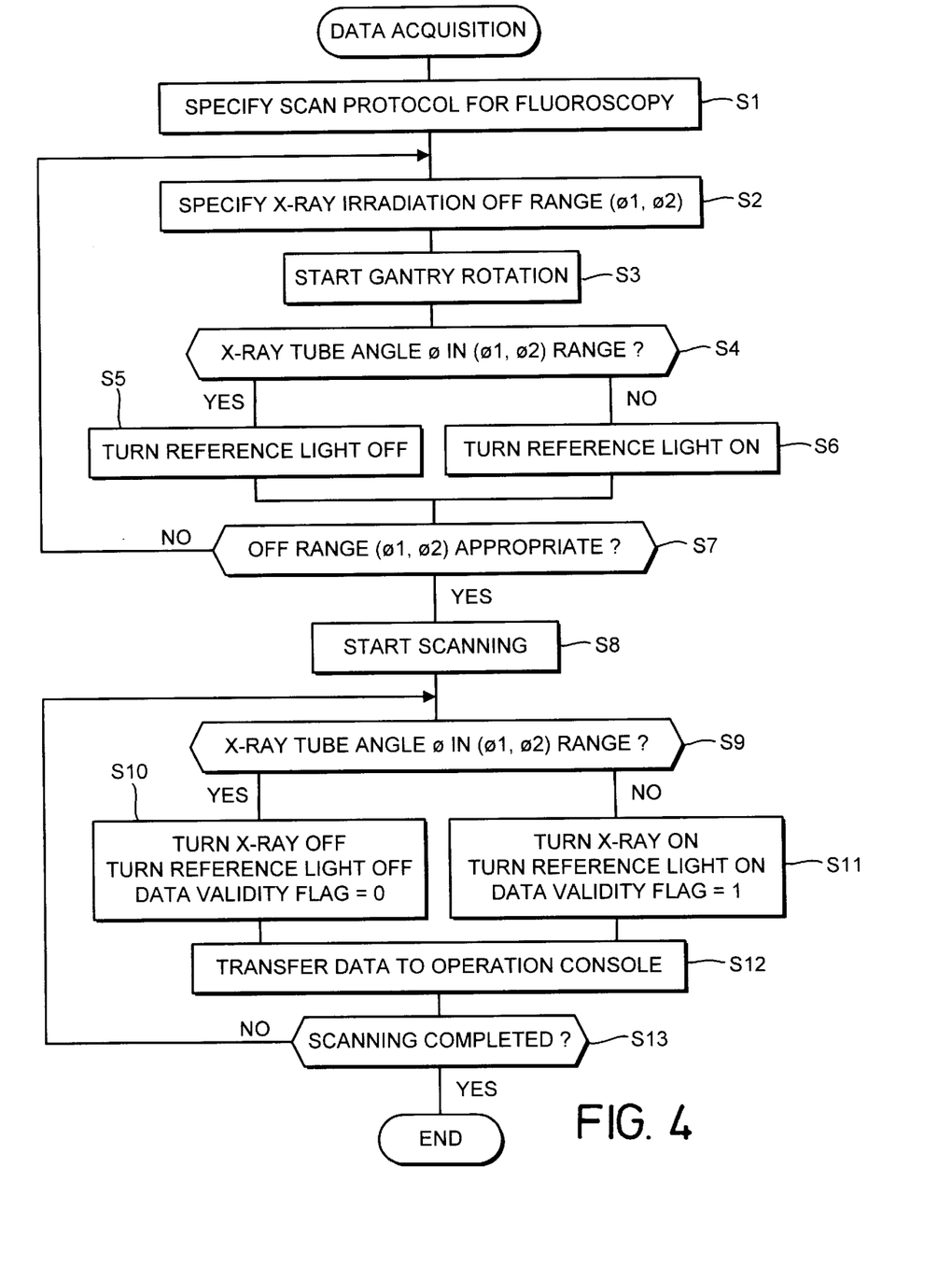
FIG. 4 is a flowchart illustrating a procedure of a data acquisition process carried out by the gantry 10 shown in FIG. 3.

FIG. 4 is a flowchart illustrating a procedure for performing data acquisition by the gantry 10.

In step S1, the operator sets a scan protocol for the fluoroscopy from the operator console 20.

In step S2, the operator sets an X-ray irradiation OFF range ($\phi 1, \phi 2$) by means of the operator console 20.

In step S3, the rotating portion in the gantry 10 starts rotating.

In step S4, it is determined whether an X-ray tube angle is in the OFF range ($\phi 1, \phi 2$) or not. If the angle $\phi$ is in the OFF range ($\phi 1, \phi 2$) then the process proceeds to step S5, while if the angle is not in the range then the process proceeds to step S6.

In step S5, the reference light 3a is turned off. Then the process proceeds to step S7.

In step S6, the reference light 3a is turned on. Then the process proceeds to step S7.

In step S7, the operator checks whether or not the light from the reference light 3a impinges upon the position of the operator's hand upon performing the fluoroscopy operation. If the hand is exposed to the light, the process returns to step S2 where the OFF range ($\phi 1, \phi 2$) is again settled. If the hand is not exposed to the light, which means that the current OFF range ($\phi 1, \phi 2$) is appropriate, then the process proceeds to step S8.

In step S8, a scan is started. That is, the rotating portion in the gantry 10 is rotated around the subject to acquire data.

In step S9, it is determined whether the X-ray tube angle is in the OFF range ($\phi 1, \phi 2$) or not. If the angle $\phi$ is in the OFF range ($\phi 1, \phi 2$) then the process proceeds to step S10 while if the angle is not in the range, the process proceeds to step S11.

In step S10, an X-ray tube current is set to "0" to halt the radiation of the X-ray. Then the reference light 3a is turned off. In addition, a data validity flag for the data having been acquired at the time is set to "0". Then the process proceeds to step S12.

In step S11, a predetermined X-ray tube current (e.g. 200 mA) is flown to energize the X-ray tube. Then the reference light 3a is turned on. In addition, the data validity flag for the data having been acquired at the time is set to "1". Then the process proceeds to step S12.

In step S12, the data having been acquired at the time is transferred to the operator console 20.

In step S13, it is determined whether a command for ending the scanning has been issued or not. If it is determined that the command is not issued, then the process returns to step S9 and the scan is continued. If the command has been issued, then the process is terminated.

Figure 5:
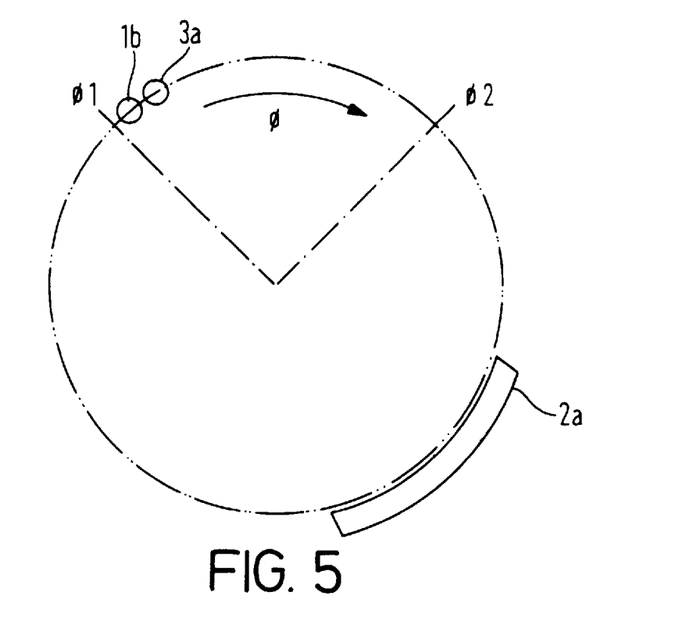
FIG. 5 is an explanatory diagram showing the condition of an X-ray tube and a reference light when the X-ray tube angle is in the OFF range.

FIG. 5 illustrates the condition of the X-ray tube 1b and the reference light 3a when the X-ray tube angle is in the OFF range (φ1,φ2). The X-ray tube 1b generates no X-ray and the reference light 3a emits no light.

Figure 6:
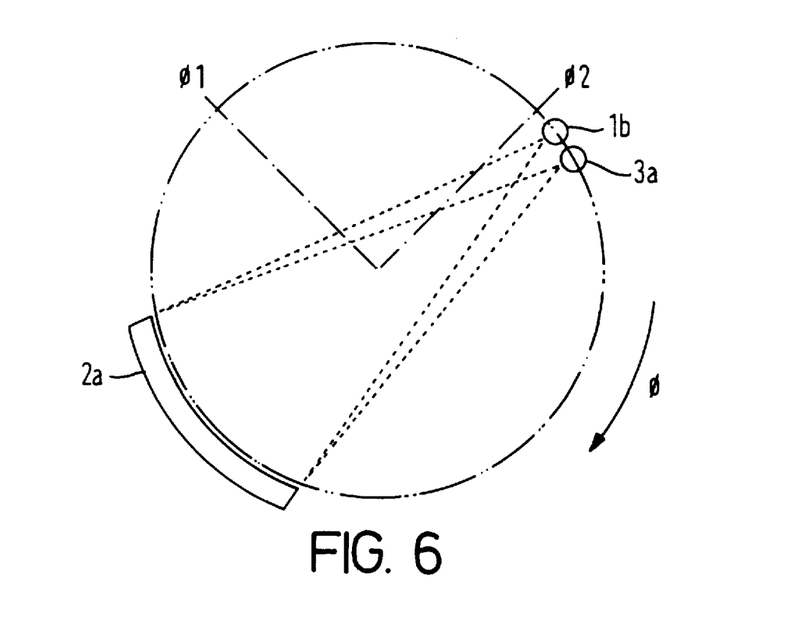
FIG. 6 is an explanatory diagram showing the condition of the X-ray tube and the reference light when the X-ray tube angle is in the ON range.

FIG. 6 illustrates the condition of the X-ray tube 1b and the reference light 3a when the X-ray tube angle φ goes out from the OFF range (φ1,φ2). The X-ray tube 1b generates X-ray and the reference light 3a emits light.

Figure 7:
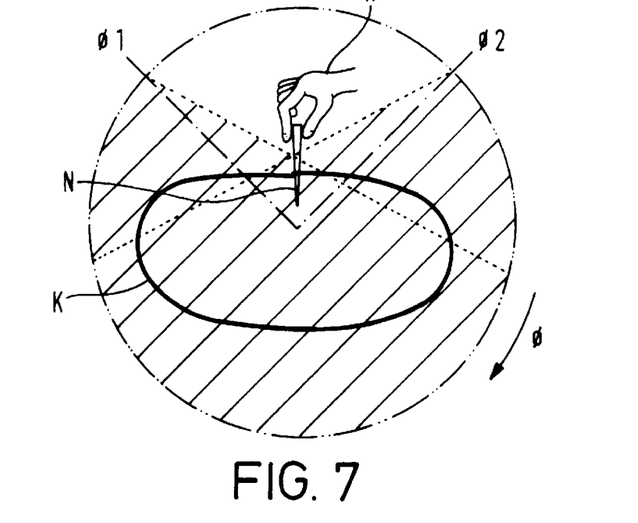
FIG. 7 is an explanatory diagram of a space through which an X-ray passes during one rotation of the X-ray tube and an X-ray detector in the X-ray CT apparatus shown in FIG. 3.

A hatched region in FIG. 7 is a space through which the X-ray passes during one rotation of the X-ray tube 1b and the X-ray detector 2a. As seen from FIG. 7, there is a space through which no X-ray passes. Likewise, no light from the reference light passes through the space where no X-ray passes. Therefore, if the operator stabs the biopsy needle into the subject K while maintaining the operator's hand at the position where the light from the reference light 3a does not pass, the operator can easily avoid the X-ray exposure.

Figure 8:
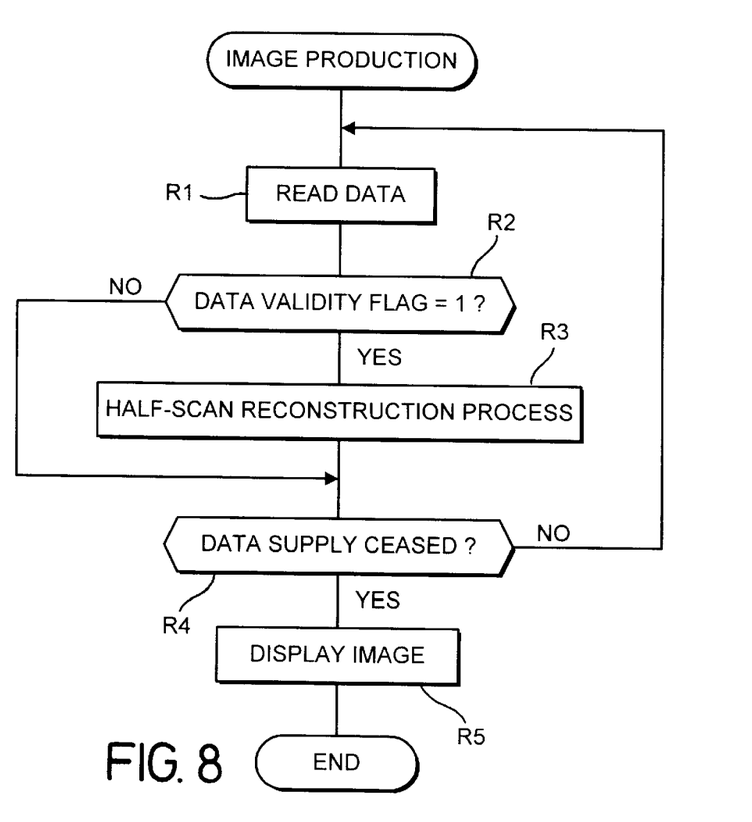
FIG. 8 is a flowchart illustrating a procedure for an image producing process at an operator console shown in FIG. 3.

FIG. 8 is a flow chart illustrating a procedure for producing an image at the operator console 20.

In step R1, the data transferred from the gantry 10 is read from the storage device.

In step R2, it is determined whether the data validity flag for the current data is "1" or not. If the flag is "1", then the process proceeds to step R3. If the flag is "0", then the process proceeds to step R4.

In step R3, the present data is utilized for a half-scan reconstruction process. The term "half-scan reconstruction process" refers to a process for reconstructing an image from data acquired during a rotation of the X-ray tube which equals to or exceeds a half rotation but stays within one rotation. Conversely, a term "full-scan reconstruction process" refers to a process for reconstructing an image from data acquired during a rotation of the X-ray tube which equals to or exceeds one rotation.

In step R4, it is determined whether the data supply is ceased or not. If it is determined that the data supply is continued, then the process returns to step R1. If it is determined that the data supply is ceased, then the process proceeds to step R5.

In step R5, the produced image is displayed and the process is terminated.

Figure 9:
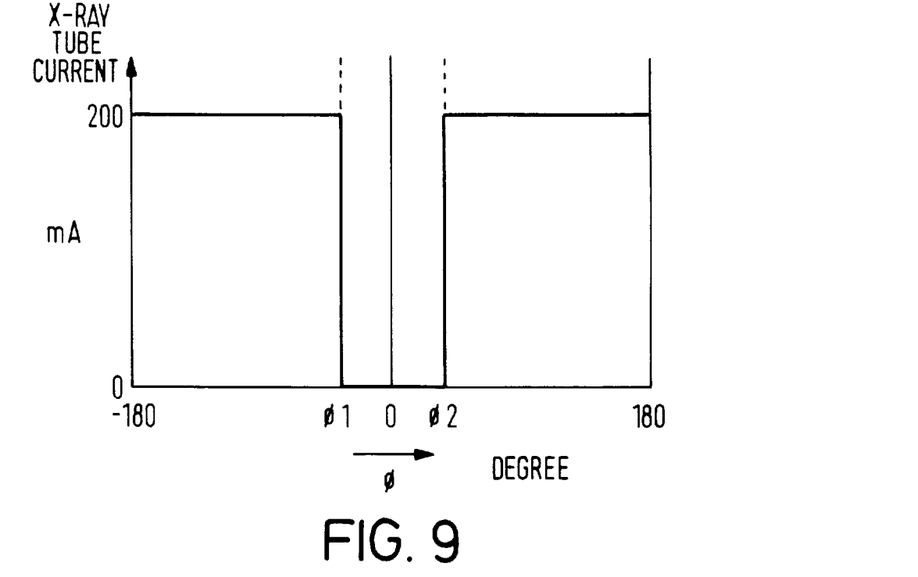
FIG. 9 is a graph illustrating how the X-ray tube current varies depending on an angle at which the X-ray tube lies.

FIG. 9 is a graph illustrating variation in the X-ray tube current depending on the X-ray tube angle φ.

The X-ray tube current is set to "0" in the OFF range (φ1,φ2) and set to a predetermined X-ray tube current (200 mA in the case of FIG.7) in a range other than that range.

According to the above X-ray CT apparatus 100, when the operator carries out the fluoroscopy operation, the operator can place his own hand at the position where the light from the reference light 3a does not pass. Thus, the operator can easily avoid the X-ray exposure. Moreover, the X-ray radiation dose is set to relatively high in the range other than the OFF range (φ1,φ2). Therefore, data with a good S/N ratio can be acquired and an image of high quality can be obtained.

Figure 10:
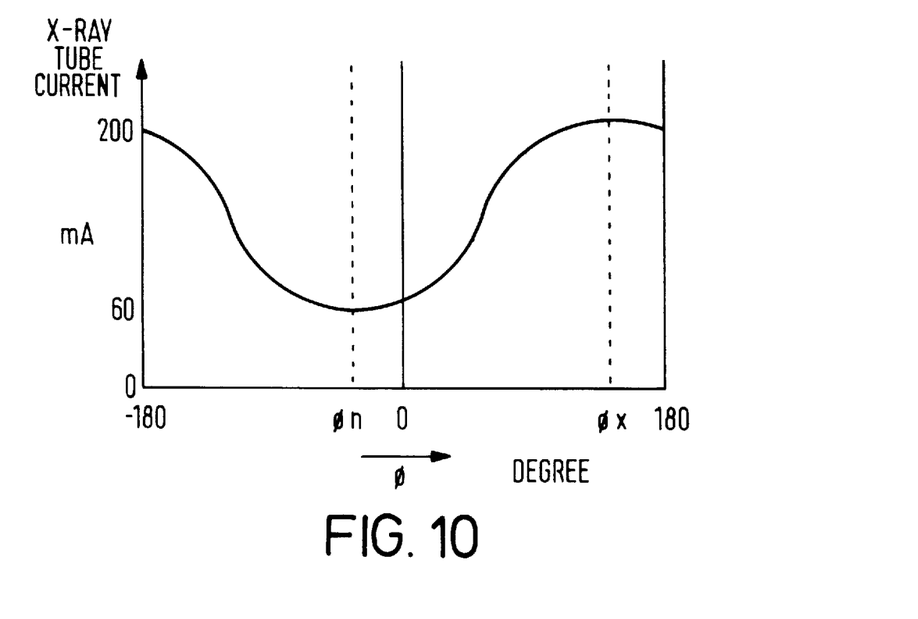
FIG. 10 is another graph illustrating how the X-ray tube current varies depending on an angle at which the X-ray tube lies.

While in the above embodiment turning the X-ray tube on or off at the steps of S10 and S11 in FIG. 10 is carried out by supplying and ceasing the electric current to the X-ray tube, a shutter or the like may be provided on a collimator aperture to selectively pass or block the X-ray radiation so that turning the X-ray tube on or off is carried out.

Further, while in the above-described embodiments data acquisition is selectively carried out depending on the angular range of the X-ray tube in which the X-ray radiation dose is increased to acquire data, the data acquisition may be carried out throughout the whole angular range of the X-ray tube to perform the full-scan reconstruction. That is, if the operator specifies a maximum value of the X-ray tube current (200 mA in the case of FIG. 10) and the corresponding angle φx along with a minimum value of the X-ray tube current (60 mA in the case of FIG. 10) and the corresponding angle φ n, then, as shown in FIG. 10, the X-ray tube current is smoothly changed in accordance with a function (e.g. a trigonometric function) on which the above specified points lie. In this case, the full-scan reconstruction process can be carried out.

According to the X-ray CT apparatus which have been described so far, the X-ray radiation dose becomes decreased when the operator's hand would otherwise be directly exposed to the X-ray radiation, and the X-ray radiation dose becomes increased when the operator's hand is not directly exposed to the X-ray radiation. Therefore, it is possible to protect the operator's hand from direct exposure to the X-ray radiation owing to the shade of the subject while collecting data with a good SIN ratio and obtaining an image of high quality.

Furthermore, the operator can accurately specify an angular range in which the X-ray exposure is decreased with the aid of the light. Also, the operator can easily be informed of a position where the hand will be less exposed to the X-ray radiation.

Although several embodiments have been described so far, various changes and modifications could be effected on the embodiments of the present invention without departing from the spirit or scope of the present invention. Further, it should be understood that the present invention is not limited to the specific embodiments described in the specification, and all variations coming from the appended claims are intended to be embraced in the present invention.

What is claimed is:

1. A fluoroscopy method for obtaining an image of a subject using a rotating X-ray source and corresponding detector with the subject positioned therebetween and a processing means; said method comprising the steps of:

determining a particular angular range within which a human operator is exposed to X-ray emitted from said x-ray source;

storing data of said particular angular range in said processing means;

controlling radiation dosage emitted by said X-ray source so that a low dosage is emitted by said X-ray source when direction of X-ray emitted from said source is within said particular angular range and a normal radiation dosage is emitted when direction of X-ray emitted from said X-ray source is outside said particular angular range; and causing a light source located close to said X-ray source to emit light of one intensity when said direction of X-ray emitted from said x-ray source is within said particular angular range, and of another intensity when said direction of X-ray emitted from said X-ray source is outside said particular angular range, so that the human operator avoids exposure to overdosage of X-ray radiation.

2. An X-ray CT apparatus, comprising:

an X-ray source means for emitting X-rays in different directions;

an X-ray detector for detecting X-rays passed through a subject;

means for rotating said X-ray source means and said X-ray detector around said subject being examined;

means for determining a particular angular range of directions of X-ray emitted by said X-ray source means at which an operator would be exposed needlessly to the X-ray;

storage means for storing information of said particular angular range;

means for controlling power to said X-ray source means so that based on said information of said particular angular range stored in said storage means power to said X-ray source means will cause said X-ray source means to supply a low amount of radiation which would not be harmful to the operator when the direction of X-ray emission is within said particular angular range, and to supply an amount of radiation sufficient to examine said subject when said direction of X-ray emission is outside of said particular angular range;

light source disposed adjacent to said X-ray source means; and means for controlling amount of light emitted by said light source to be of one value when said direction of X-ray emission by said X-ray source means is within said particular angular range, and to be of another value when said direction of X-ray emission by said X-ray source means is outside of said particular angular range.

3. The apparatus of claim 2, wherein said means for controlling power comprises means for applying a data validity flag which makes data invalid to data acquired when said direction of X-ray emission is in said particular angular range; and means for applying another validity flag which makes data valid to data acquired when said direction of X-ray emission is outside of said particular angular range.

4. The apparatus of claim 2, further comprising means for carrying out data acquisition when said direction of X-ray emission is in said particular angular range, means for carrying out data acquisition when said direction of X-ray emission is outside of said particular angular range; and means for changing amount of power supplied to said X-ray source means depending on said particular angular range at which said direction of X-ray emission is at so as to smooth transition between data acquisition when said direction of X-ray emission is within said particular angular range and when said direction of X-ray emission is outside said particular angular range.

5. The apparatus of claim 2, wherein said X-ray source means comprises a collimator aperture through which said X-rays are emitted, and means for selectively passing X-rays through said collimator aperture.

* * * * *